United States Patent [19]

Snoke et al.

[11] Patent Number: 5,531,687
[45] Date of Patent: *Jul. 2, 1996

[54] STEERABLE CATHETER

[75] Inventors: Phillip J. Snoke, Atlanta; David S. Rowley; David G. Lincoln, both of Smyrna; Kirk W. Charles, Austell, all of Ga.

[73] Assignee: Catheter Imaging Systems, Atlanta, Ga.

[ * ] Notice: The term of this patent shall not extend beyond the expiration date of Pat. No. 5,342,299.

[21] Appl. No.: 367,105

[22] Filed: Dec. 30, 1994

Related U.S. Application Data

[60] Continuation of Ser. No. 279,500, Jul. 22, 1994, Pat. No. 5,437,636, which is a division of Ser. No. 908,403, Jul. 6, 1992, Pat. No. 5,342,299.

[51] Int. Cl.$^6$ .................................................. A61M 37/00
[52] U.S. Cl. ........................... 604/95; 600/131; 600/146
[58] Field of Search ............................... 604/95; 600/114, 600/129, 131, 139, 146, 147; 128/772, 657–658

[56] References Cited

U.S. PATENT DOCUMENTS

| | | |
|---|---|---|
| 3,470,876 | 10/1969 | Barchilon . |
| 3,605,725 | 9/1971 | Bentov . |
| 3,892,228 | 7/1975 | Mitsui . |
| 4,421,106 | 12/1983 | Uehara . |
| 4,483,326 | 11/1984 | Yamaka et al. . |
| 4,737,142 | 4/1988 | Heckele . |
| 4,748,969 | 6/1988 | Wardle . |
| 4,750,475 | 6/1988 | Yoshihashi . |
| 4,776,844 | 10/1988 | Ueda . |
| 4,791,912 | 12/1988 | Tashiro . |
| 4,905,666 | 3/1990 | Fukuda . |
| 4,930,521 | 6/1990 | Metzger et al. . |
| 4,934,340 | 6/1990 | Ebling et al. . |
| 4,954,129 | 9/1990 | Giuliani et al. . |
| 4,972,828 | 11/1990 | Ito . |
| 4,979,496 | 12/1990 | Komi . |
| 4,983,165 | 1/1991 | Loiterman . |
| 4,986,258 | 1/1991 | Cho et al. . |
| 4,996,974 | 3/1991 | Ciarlei . |
| 5,143,475 | 9/1992 | Chikama . |
| 5,167,221 | 12/1992 | Chikama . |
| 5,197,649 | 3/1993 | Bessler et al. . |
| 5,199,417 | 4/1993 | Muller et al. . |
| 5,199,950 | 4/1993 | Schmitt et al. . |
| 5,273,535 | 12/1993 | Edwards et al. ........................... 604/95 |
| 5,275,151 | 1/1994 | Shockey et al. . |
| 5,342,299 | 8/1994 | Snoke et al. . |
| 5,344,397 | 9/1994 | Heaven et al. . |

FOREIGN PATENT DOCUMENTS

| | | |
|---|---|---|
| 0370158 | 5/1990 | European Pat. Off. . |
| 0489937 | 6/1992 | European Pat. Off. . |
| 990417 | 9/1951 | France . |
| 2655548 | 6/1991 | France . |
| 1213571 | 3/1966 | Germany . |
| WO88/00810 | 2/1988 | WIPO . |
| WO91/11213 | 8/1991 | WIPO . |

*Primary Examiner*—Corrine M. McDermott
*Attorney, Agent, or Firm*—Bell, Seltzer, Park & Gibson

[57] ABSTRACT

A catheter for use in body vessels or cavities has a housing of such size as to be readily held in the hand of a user and elongate tube means having one end connected to the housing and extending outwardly therefrom and being formed of material of such a stiffness so as to maintain the elongate tube means in straight condition in the absence of an external force applied thereto, an outer end portion of the elongate tube means being flexible. Guide wires are connected to the housing by the inner ends thereof and extend outwardly therefrom through the elongate tube means. The outer ends of the guide wires are connected to the flexible outer end portion of the elongate tube means. Guide wire control means is carried by the housing and cooperates with the inner end portions of the guide wires for controlling the angular attitude of the flexible outer end portion of the elongate tube means.

13 Claims, 8 Drawing Sheets

STEERABLE CATHETER

RELATED APPLICATIONS

This application is a continuation of U.S. patent application Ser. No. 08/279,500 filed Jul. 22, 1994 now U.S. Pat. No. 5,437,636 which is a division of U.S. patent application Ser. No. 07/908,403 now U.S. Pat. No. 5,342,299, filed Jul. 6, 1992, and is related to copending U.S. patent application Ser. Nos. 08/308,142 filed Sep. 19, 1994; 07/963,431 filed Oct. 19, 1992; 07/970,490 filed Nov. 2, 1992; and Issued U.S. Pat. No. 5,354,266 filed on Sep. 30, 1993, formerly U.S. patent application Ser. No. 08/129,331.

FIELD OF THE INVENTION

This invention relates to medical catheters, and more particularly to steerable catheters for inserting into body vessels or cavities.

BACKGROUND OF THE INVENTION

Various commercially available catheters and endoscopes exist for introducing into the body vessels and cavities a variety of surgical tools, fluids, and other materials, such as radiographic contrast materials, angioplasty balloons, fiberoptic scopes, laser lights, and cutting instruments. Also, various techniques and systems have been developed for guiding or steering the catheters in the body vessels and cavities for use of these tools, fluids, and other materials.

Examples of such guiding or steering techniques and systems for catheters may be seen in U.S. Pat. No. 4,983,165 to Loiterman entitled "Guidance System For Vascular Catheter Or The Like," U.S. Pat. No. 4,776,844 to Ueda entitled "Medical Tube," U.S. Pat. No. 4,934,340 to Ebling et al. entitled "Device For Guiding Medical Catheters and Scopes," U.S. Pat. No. 4,930,521 to Metzget et al. entitled "Variable Stiffness Esophageal Catheter," U.S. Pat. No. 3,470 to Barchilon entitled "Dirigible Catheter," U.S. Pat. No. 3,605,725 to Bentov entitled "Controlled Motion Devices," and the Patent Cooperation Treaty ("PCT") Patent Application No. PCTW088/00810 of Tenerz et al. entitled "Guide For Mechanical Guiding Of A Catheter In Connection With Cardio And Vessel Examination." These catheters, however, failed to give the physician or other operator sufficient control of the distal end of the catheter and made it difficult to manipulate the distal end for specific isolation on particular sections of the body vessel or cavity.

Other steerable catheters or systems have been made to try to give the physician control of the use of the catheter during surgical procedures wherein fluids and the various tools are needed for the operation by providing a flexible tube for controlling the direction of movement of the distal end of the catheter. Examples of these other attempts may be seen in the PCT Patent Application No. PCTW091/11213 of Lundquist et al. entitled "Catheter Steering Mechanism," European Patent Application No. 370,158 of Martin entitled "Catheter For Prolonged Access," and U.S. Pat. No. 4,737,142 to Heckele entitled "Instrument For Examination And Treatment Of Bodily Passages." These devices, however, still failed to provide the control and manipulation of the catheter needed for use with the surgical tools and fluids required for an operation.

Therefore, there is still a need for a steerable catheter that provides the control and manipulation of the catheter for simultaneous use with the surgical tools, such as fiberoptic scopes or the like, and fluids needed for medical operations to thereby allow the physician to positionally locate and isolate problem areas within the body vessel or cavity.

SUMMARY OF THE INVENTION

It is therefore an object of the present invention to provide a catheter having improved steering.

It is also an object of the present invention to provide a catheter that allows the physician or operator to have more control over the distal end therein and provides feedback to the physician of the angular attitude of the distal end.

It is another object of the present invention to provide a catheter having a housing of such a size as to be readily held in the hand of the user for the physician or operator to control the steering of the catheter while simultaneously providing access to the lumen within the catheter for various surgical tools or fluids.

It is a further object of the present invention to provide a catheter having a fiberoptic scope sheath adapted to engage the housing of the catheter for inserting a fiberoptic scope into a lumen of the catheter.

These and other objects, features, and advantages of the present invention are provided in a catheter having more controlled movement in the distal end and having feedback on this movement to the catheter user the details of which are disclosed in the detailed description and the enclosed drawings.

In accordance with the present invention, a steerable catheter is provided for use in body vessels or cavities. The steerable catheter comprises a housing of such a size as to be readily held in the hand of the user. The catheter also has elongate tube means having one end connected to the housing and extending outwardly therefrom and being formed of material of such a stiffness so as to maintain the elongate tube means in a substantially straight condition in the absence of an external force applied thereto. An outer end portion of the elongate tube means is flexible. Guide wires are connected to the housing by the inner ends thereof and extend outwardly therefrom through the elongate tube means. The outer ends of the guide wires are connected to the flexible outer end portion of the elongate tube means. Guide wire control means is carried by the housing and cooperates with the inner end portions of the guide wires for controlling the angular attitude of the flexible outer end portion of the elongate tube means. The guide wires and control means cooperate so as to limit the angular attitude of the flexible outer end portion of the elongate tube means to angular adjustments in a common plane extending generally parallel to the upper surface of the housing and wherein the angular adjustment of the flexible outer end portion of the elongate tube means in all other planes is obtained by rotation of the user's hand, so that more control of the attitude of the flexible outer end portion of the elongate tube means is obtained during use of the catheter.

At least one lumen extends longitudinally from the outer end of the elongate tube means and into the housing. The housing has at least one access port to the lumen. A fiberoptic sheath is adapted to be attached to the access port of the housing for inserting a fiberoptic scope or the like through the access port and into the lumen. A proximal tube is also provided which extends outwardly from the housing.

DESCRIPTION OF A PREFERRED EMBODIMENT

The present invention now will be described more fully hereinafter with reference to the accompanying drawings in which a preferred embodiment of the invention is shown. Like numbers refer to like elements throughout.

Figure 1:
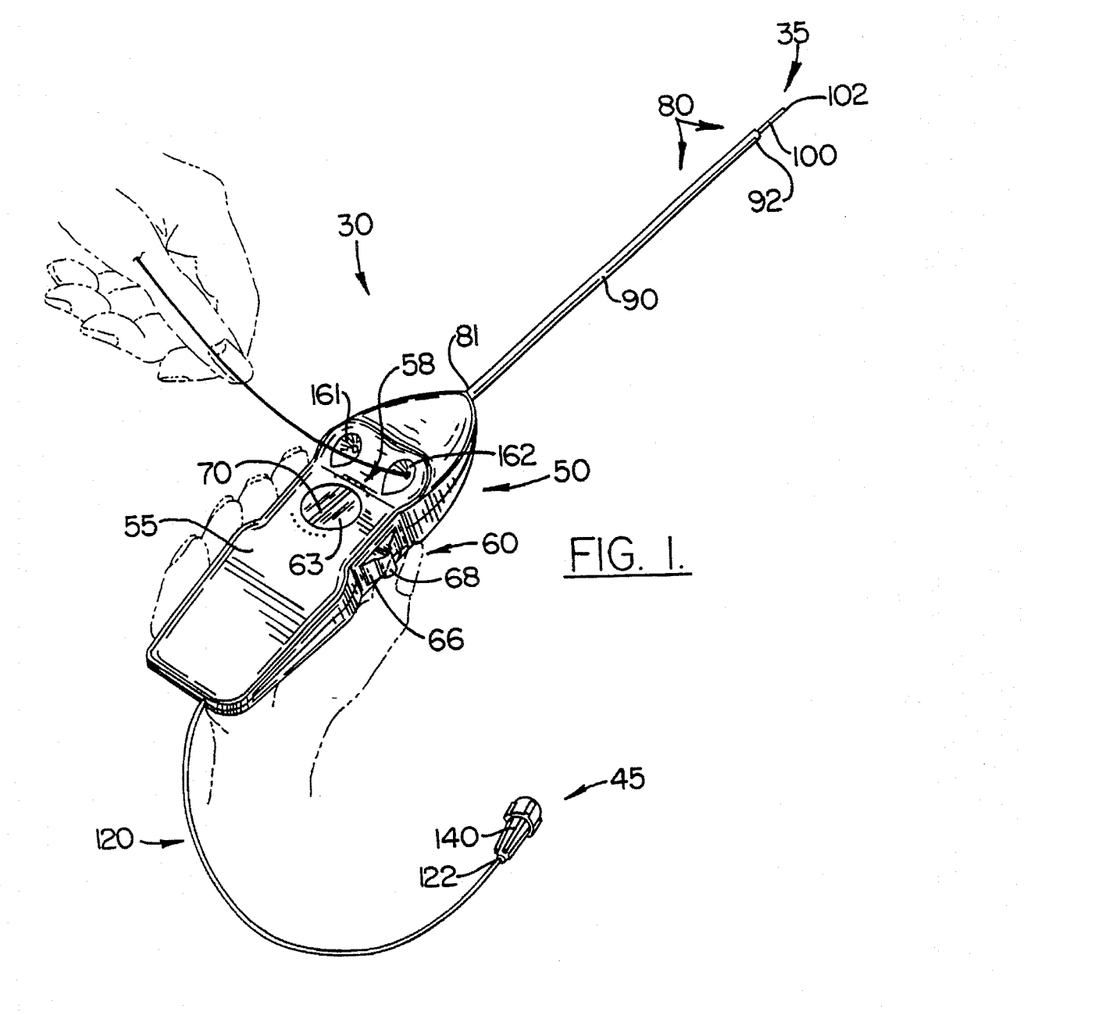
FIG. 1 is an environmental view of the steerable catheter being held by the hand of the catheter operator while simultaneously having a fiberoptic scope inserted into an access port in the housing of the catheter according to a preferred embodiment of the present invention.

Referring now to FIG. 1, shown is an environmental view of a preferred embodiment of the steerable catheter 30 having distal 35 and proximal 45 ends according to the present invention. The steerable catheter 30 is being held in the hands of a catheter operator, such as a physician. The steerable catheter 30 has a housing 50, an elongate tube means 80, and a proximal tube 120. The elongate tube means 80 has a first tube and a second tube 100. Two lumens 94, 95 (FIG. 7) extend longitudinally from the distal end 35 of the catheter, through the first 90 and second 100 tubes of the elongate tube means 80 and into the housing 50. The first tube 90 is formed of a material of such a stiffness so as to maintain the first tube 90 in a substantially straight condition in the absence of an external force applied thereto. It is understood that a substantially straight condition would generally mean that the tube in not generally bendable but a certain amount of arc may occur under some conditions or application of an external force as previously mentioned. The second tube 100 is generally more flexible than the first tube 90. The elongate tube means 80 in this embodiment comprises the first tube 90 and the second tube 100, but this invention would include using one, two, or more tubes.

The housing 50 is of such a size as to be readily held in the hand of the catheter operator or other user. Access ports 161, 162 are provided in the housing 50 for accessing the two lumens 94, 95 within the elongate tube means 80. One end 9i of the first tube 90 is connected to the housing 50 and then the first tube 90 extends outwardly therefrom. The second tube 100, in turn, extends longitudinally from a second end 92 of the first tube 90. An end 102 of the second tube 100 forms the distal end 35 of the steerable catheter 30. The proximal tube 120 extends longitudinally through the housing 50 and extends longitudinally from the housing 50. A first end 121 (not shown in this view) of the proximal tube 120 accesses the first end 91 of the tube within the housing 50. The connector 140 attached to the second end 122 of the proximal tube 120 forms the proximal end 45 of the steerable catheter 30.

A control wheel 60 is mounted to the housing 50 to aid in guiding and steering the distal end 35 of the steerable catheter 30. The control wheel is generally circular in shape and has a front end a back end 62, a top end 63, a bottom end 64, and two side ends 66, 67. Lobes 68, 69 are located on the two side ends 66, 67 of the control wheel. A tip direction indicator 70 is located on a top end 63 of the control wheel 60. The tip direction indicator 70 lies in a longitudinal direction with respect to the upper surface 55 of the housing 50. The distal end 35 of the steerable catheter 30 moves by rotating the control wheel 60 via the lobes 68, 69 on the side ends 66, 67 of the control wheel 60. The tip direction indicator 70, in turn, rotates clockwise and counter-clockwise to a position indicating the direction and angular attitude of the distal end 35. Position markers 58 are located on the upper surface 55 of the housing 50 around the top end 63 of the control wheel 60 to thereby mark the relative angular attitude of the distal end 35 of the steerable catheter 30 as it is being deflected and controlled.

Figure 2:
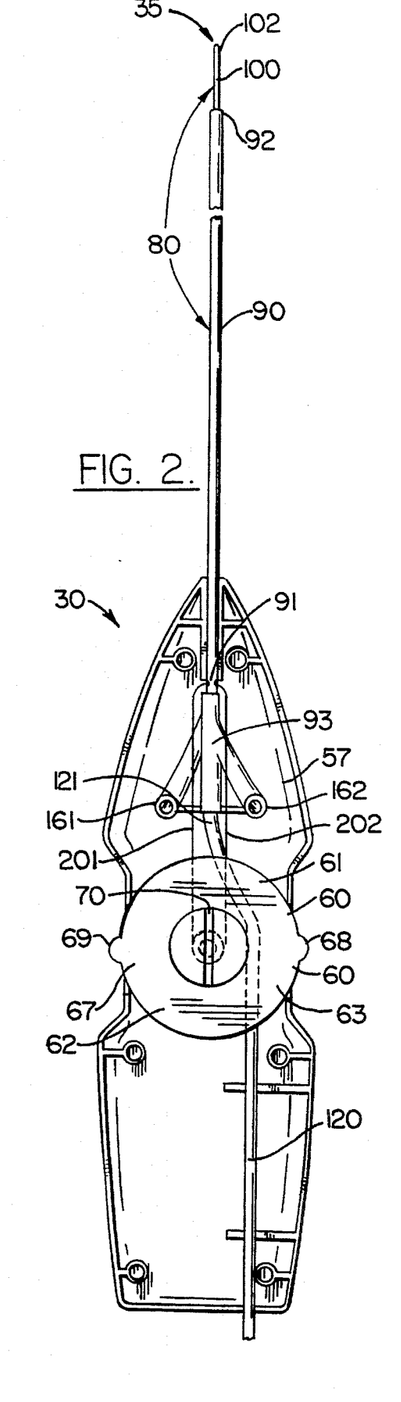
FIG. 2 is a top plan view of the steerable catheter with the top cover removed from the housing and with parts broken away for clarity.
Figure 3:
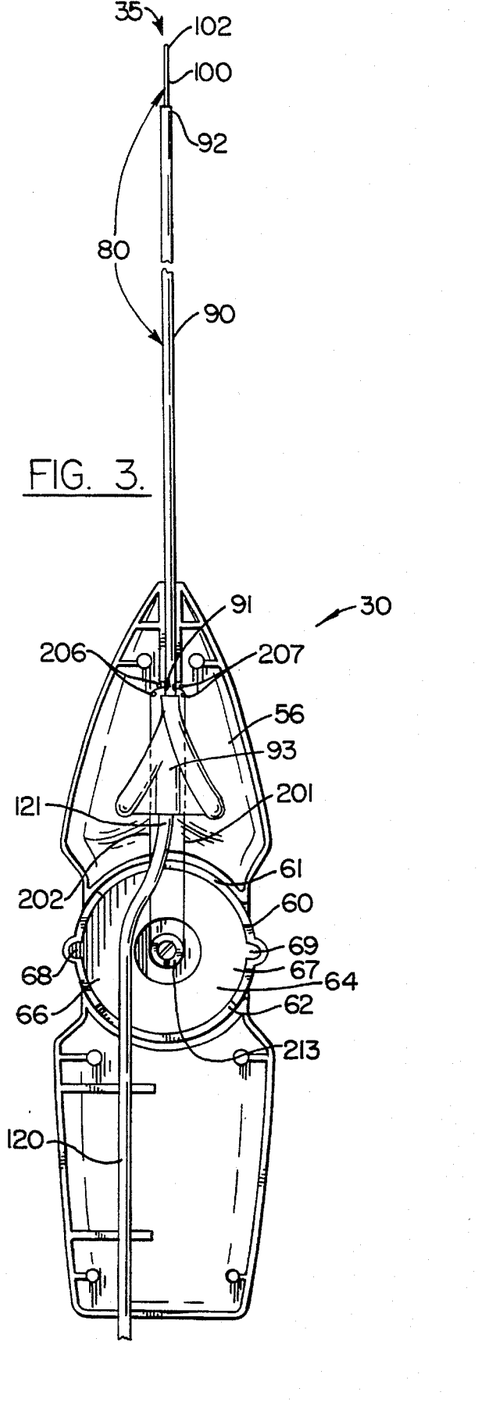
FIG. 3 is a bottom plan view of the steerable catheter with the bottom cover removed from the housing and with parts broken away for clarity.

FIGS. 2–7 illustrate the internal construction of the steerable catheter 30 according to the invention. In FIGS. 2 and 3, the top cover 56 and bottom cover 57 are each respectively removed from the housing 50 to clarify the construction therein. These views illustrate the attachment of the first end 121 of the proximal tube 120 to the first end 91 of the first tube 90. These views also illustrate the placement of a portion of the proximal tube 120 within the housing 50.

Figures 4, 5, 6, 7:
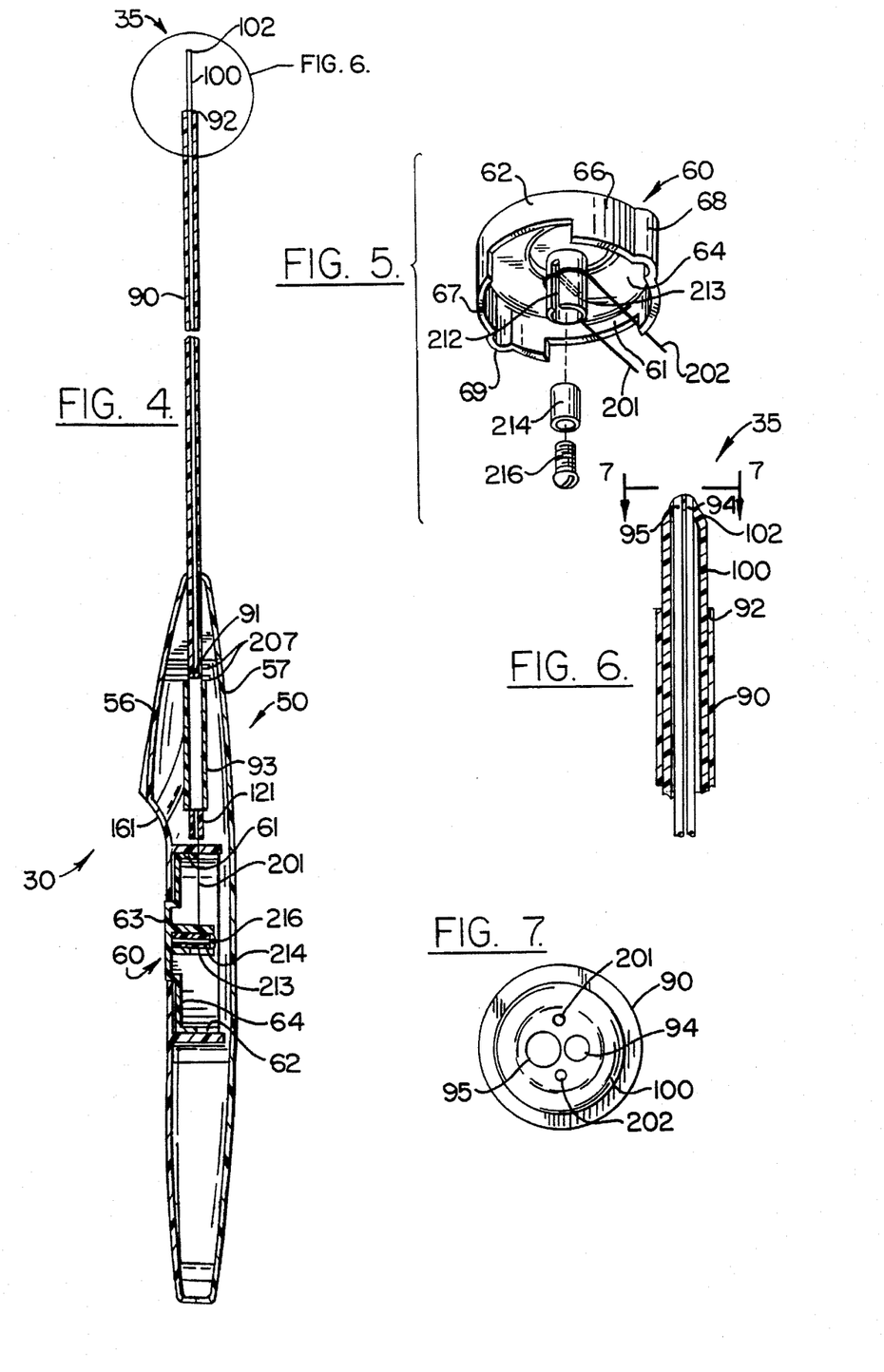
FIG. 4 is a side cross-sectional view of the steerable catheter according to the preferred embodiment of the present invention.
FIG. 5 is an exploded view of the control wheel of the housing according to the preferred embodiment of the present invention.
FIG. 6 is an enlarged view of the flexible outer end portion of the elongate tube means of the steerable catheter taken from the circled portion of FIG. 4 and rotated ninety (90) degrees.
FIG. 7 is an enlarged front view of the flexible outer end portion of the elongate tube means of the steerable catheter taken along line 7—7 of FIG. 6.

The side cross-sectional view of FIG. 4 further illustrates the connection of the ends of the proximal tube 120, the first tube 90, and the second tube 100 inside and outside the housing 50. This view also illustrates the mounting of the control wheel within the housing 50 and with respect to the proximal tube 120.

Referring again to FIGS. 2 and 3, two guide wires 201, 202 longitudinally extend from the distal end 35 of the steerable catheter 30 through the second tube 100 and through the first tube 90. The guide wires 201, 202, in turn, extend from the first end of the first tube 90, around wire guide members 207, and attach to the control wheel 60. Hence, when the control wheel 60 rotates, the guide wires 201, 202 move to thereby provide movement and control of the distal end 35 of the steerable catheter 30.

FIG. 5 is an exploded perspective view of the control wheel 60 showing the connection of the guide wires 201, 202 therein. The inner ends of the guide wires 201, 202 within the housing 50 wrap around a circular hub base 213 on the bottom end 64 of the control wheel 60. The guide wires 201, 202 are secured to a wire receptacle 212 in the hub base 213 by a sleeve 214 and screw 216. The outer ends of the guide wires 201, 202 are sonic welded to the second tube 100. Plugs in the second tube 100 may also be used to connect the guide wires 201, 202 at outer ends.

This particular arrangement of the wires with the control wheel makes the wheel self-locking as the wheel rotates within the housing. Friction (f) is caused by the wire pull (W) acting as a normal force on the housing 50. Since the desire of the user is that the wheel not freely rotate during use, this requirement can be satisfied if the moment due to the wire pull (M1= W×r, where r is the radius of the hub base) does not exceed the moment due to friction (M2=f×R, where R is the radius of the control wheel 60). Since f= μ×W (where μ is the coefficient of friction), then by substitution M2= μ×W×R. If the moment due to the wire pull (M1) is less than the moment due to friction (M2), then W×r< μ×W×R. So if r/R< μ then the wheel will not rotate by wire pull.

The control wheel 60 and the inner ends of the guide wires 201, 202 cooperate as described to control the angular attitude 220 of the second tube 100. The control wheel 60 and guide wires 201, 202 cooperate to limit the angular attitude of the second tube 200 to angular adjustments in a common plane extending generally parallel to the upper surface of the housing 50. The angular adjustments 220 in all other planes is obtained by rotation of the user's hand so that more control of the attitude of the second tube 200 is obtained during use of the catheter 30. Detents are also located in the control wheel at zero (0), fifteen (15), and thirty (30) degrees with respect to the angular attitude 220 of the distal end 35 of the catheter 30. These detents, however, may not be used at all or be located at various angular attitude 220 positions.

FIGS. 6 and 7 illustrate the distal end 35 of the steerable catheter 30 and the construction of the guide wires 201, 202 and lumens 94, 95 therein. FIG. 6 is an enlarged view of the flexible tube portion and the first tube 90 taken from the circled portion of FIG. 4. FIG. 7 is a front view of the distal end 35 of the steerable catheter 30 taken along line 7—7 of FIG. 6. Along with the guide wires 201, 202, the second tube 200 and the first tube 90 of the elongate tube means 80 have two working lumens 94, 95 extending longitudinally from the distal end 35, through the second tube 200, through the first tube 90, and into the housing 50. The lumens 94, 95 provide access for a variety of surgical tools, fluids, and other materials, such as radiographic contrast materials, angioplasty balloons, fiberoptic scopes, laser lights, and cutting instruments. This access enables the physician or catheter operator to simultaneously steer the catheter while also using the various surgical tools, fluids, and other materials as needed in the procedure.

Figure 8:
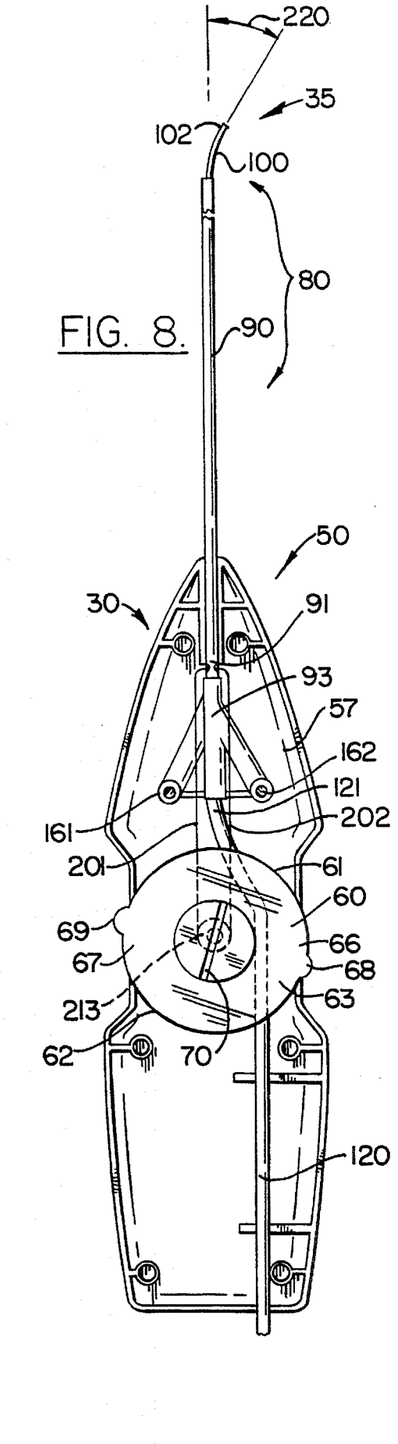
FIG. 8 is a top plan view of the steerable catheter with the top cover removed from the housing and with the control wheel rotated so as to move the flexible outer end portion of the elongate tube means of the steerable catheter to the right.
Figure 9:
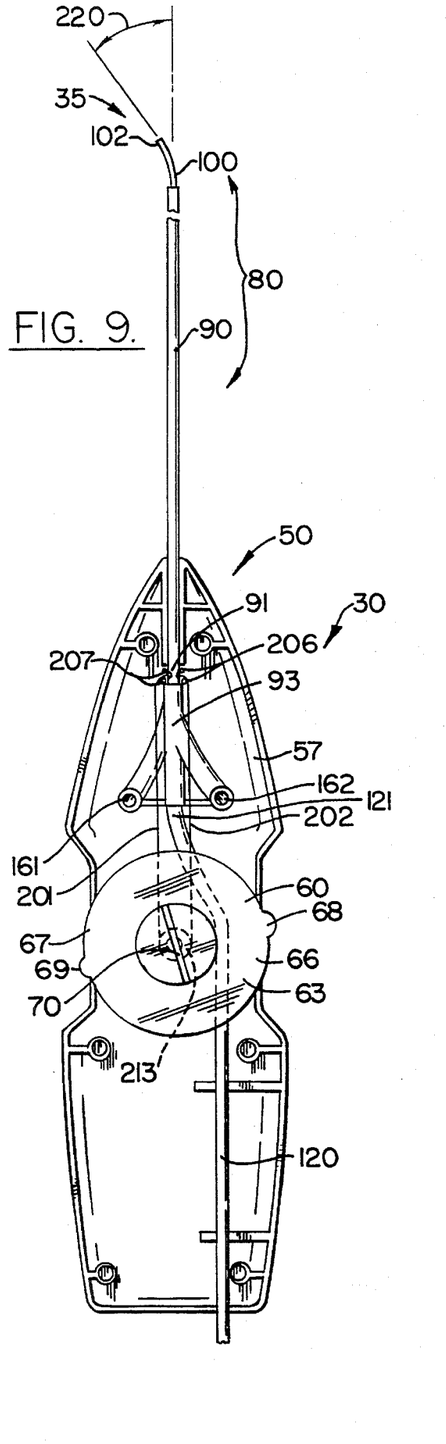
FIG. 9 is a top plan view of the steerable catheter with the top cover removed from the housing and with the control wheel rotated so as to move the flexible outer end portion of the steerable catheter to the left.

FIGS. 8 and 9 are shown to further illustrate the controlled movement of the distal end 35 of the steerable catheter 30 via rotation of the control wheel 60. FIGS. 8 and 9, similar to FIG. 2, are taken from a top view with the top cover 58 of the housing 50 removed therefrom and with parts broken away for clarity. As can be seen from FIGS. 8 and 9, the distal end 35 moves horizontally toward the direction of the tip direction indicator 70 located on a top end 63 of the control wheel 60. The hand of the operator rotates the control wheel 60 by movement of the lobes 68, 69 on the side ends 66, 67 thereof. The rotation of the control wheel 60 via the lobes 68, 69 causes tension in one direction or the other to be place upon the guide wires 201, 202 wrapped around the hub base 213 to thereby move the distal end 3S a controlled or limited amount. The construction of the control wheel 60 and the guide wires 201, 202 is such that the angular attitude 220 of the distal end 35 is no greater than thirty (30) degrees.

Figures 10, 11, 12:
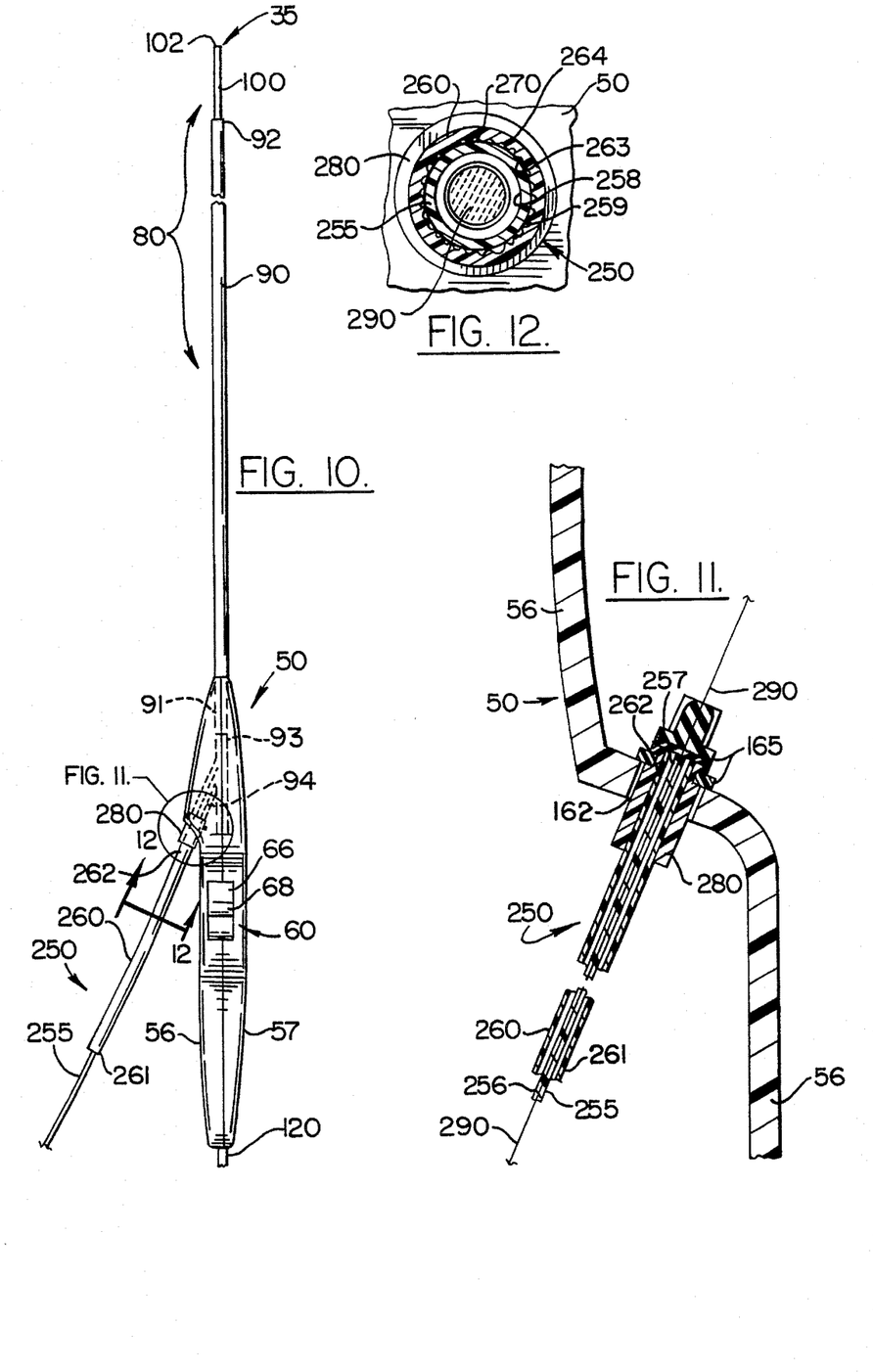
FIG. 10 is a side view of the steerable catheter having the fiberoptic scope sheath attached to an access port in the housing according to a preferred embodiment of the present invention.
FIG. 11 is an enlarged view of the circled portion of the steerable catheter having the fiberoptic scope sheath from FIG. 10 with parts broken away for clarity.
FIG. 12 is a cross-sectional view of the steerable catheter with the fiberoptic scope sheath taken along line 12—12 of FIG. 10 according to the preferred embodiment of the present invention.

Referring now to FIGS. 10–12, the fiberoptic scope sheath 250 of the preferred embodiment of the steerable catheter 30 will now be discussed. As shown in FIG. 10 with the fiberoptic scope sheath 250 enlarged for illustrative purposes, the fiberoptic scope sheath 250 connects to either of the access ports 161, 162. The fiberoptic scope sheath 250 provides feedback to the operator of the steerable catheter on the positional location of a fiberoptic scope 290 or the like when the scope 290 extends into a lumens 94, 95 of the catheter 30. A fiberoptic scope 290 generally has a small diameter and may be fragile when pushed into the body cavity or vessel. Because the fiberoptic scope 290 is not radiopaque, the scope tip location in relation to the distal end 35 of the steerable catheter 30 may be undetectable to an imaging screen supplementing the fiberoptic scope image, such as that provided by a fluoroscope or the like. A fluoroscope or the like may be used to indicate the location of the distal end 35 of the catheter 30. The fiberoptic scope sheath 250, in turn, provides imaging indication, control, and protection for the fiberoptic scope 290 when the scope 290 is used with the steerable catheter 30.

As shown in FIGS. 10 and 11, the fiberoptic scope sheath 250 essentially terminates at the access to the lumen 94 and provides the imaging indication, control, and protection discussed above. FIG. 12 is a cross-sectional view of the elongate tube means 40 having the fiberoptic scope sheath 250 thereon taken along line 12—12 of FIG. 10. The fiberoptic scope sheath 250, as seen in these views has a first sheath tube 255 with first 256 and second 257 ends, and inner 258 and outer 259 tube walls. The inner tube wall 258 of the first tube. 255 longitudinally receives the fiberoptic scope 290 through the first end 256 of the first sheath tube 255. A second sheath tube 260 having first 261 and second ends 262, and inner 263 and outer 264 tube walls longitudinally receives the first sheath tube 255. The inner tube wall 263 of the second tube 260 has ribs 270 which engage the outer tube wall 259 of the first sheath tube 255. The second end 262 of the second sheath tube 260 engages a connector 280 which is adapted to connect to one of the access ports 161, 162 in the housing 50. In turn, the fiberoptic scope 290 accesses one of the lumens 94, 95 of the steerable catheter 30 through the first sheath tube 255 and into one of the access ports 161, 162. FIG. 11 also shows a cross-sectional enlargement of seals 165 in the access ports 161, 162. The seals are formed of an elastomeric material such as silicone rubber and have a very small axial opening therethrough that permits a small object such as the fiberoptic scope 290 or the like to enter, but which otherwise prevents fluid flow in either direction, and thus protects the lumens 94, 95 from receiving contaminants or the like therein.

Figure 16:
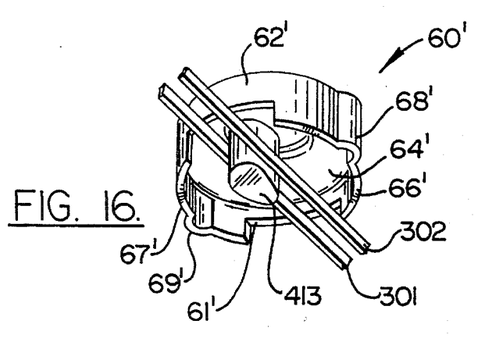
FIG. 16 is an exploded view of the control wheel according to another embodiment of the present invention.
Figure 17:
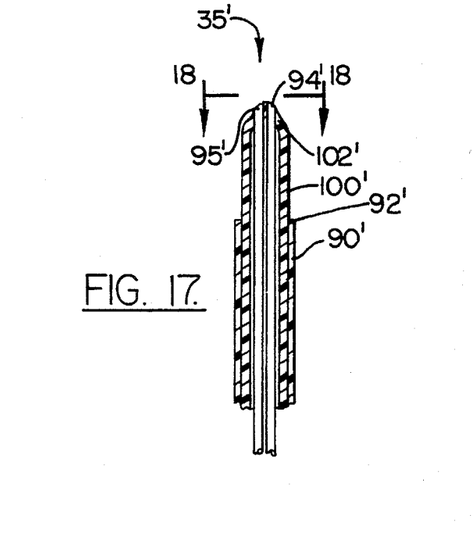
FIG. 17 is an enlarged view of the flexible outer end portion of the elongate tube means of the steerable catheter according to another embodiment of the present invention taken from the circle portion in FIG. 15 and rotated ninety (90) degrees.
Figure 18:
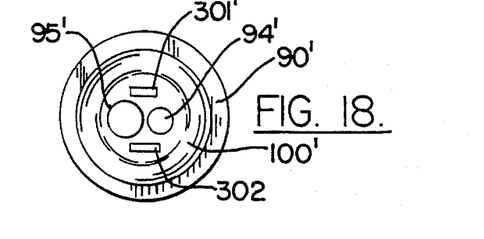
FIG. 18 is an enlarged front view of the flexible outer end portion of the elongate tube means of the steerable catheter according to another embodiment of the present invention taken along line 18—18 of FIG. 17.

FIGS. 13–20 will now be discussed to illustrate the construction of another embodiment of the steerable catheter 30' of the present invention. Similar elements in FIGS. 13–20 are labeled with prime notation corresponding to FIGS. 1–12 and are not described further herein. In FIG. 18, the front view of the distal end 35' of the steerable catheter 30, taken along line 18—18 of FIG. 17 is shown. This view shows rectangular-shaped guide wires 501, 502 instead of the circular-shaped guide wires 201, 202 of the preferred embodiment of the steerable catheter 30. Although the overall construction of the other embodiment is generally the same as a preferred embodiment, the rectangular-shaped guide wires 501, 502 provide additional control for the movement of the distal end 35' of the catheter 30'.

Figure 13:
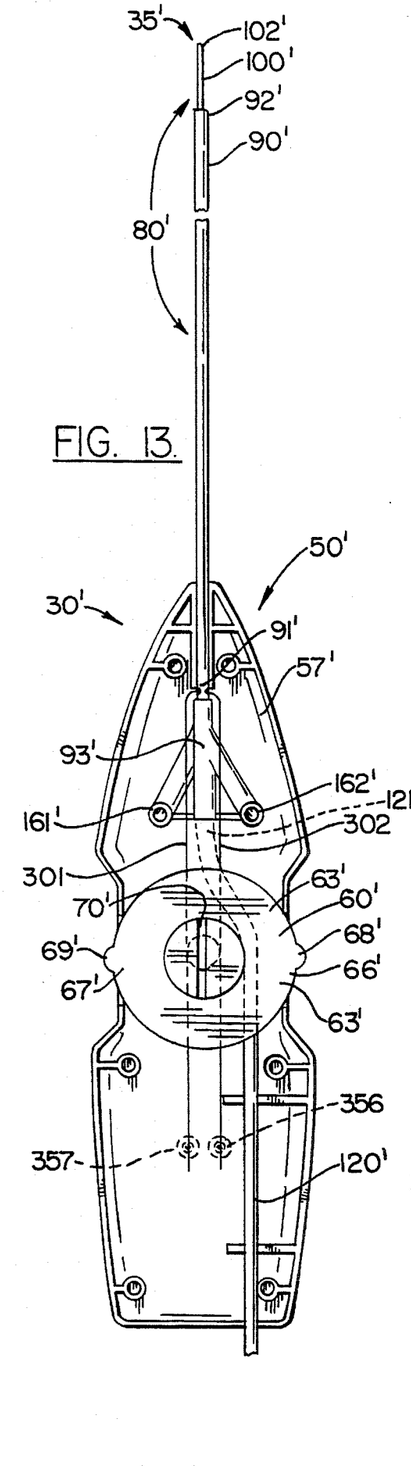
FIG. 13 is a top plan view of the steerable catheter according to the present invention with the top cover removed from the housing and with parts broken away for clarity illustrating another embodiment of the control means for the catheter.
Figure 14:
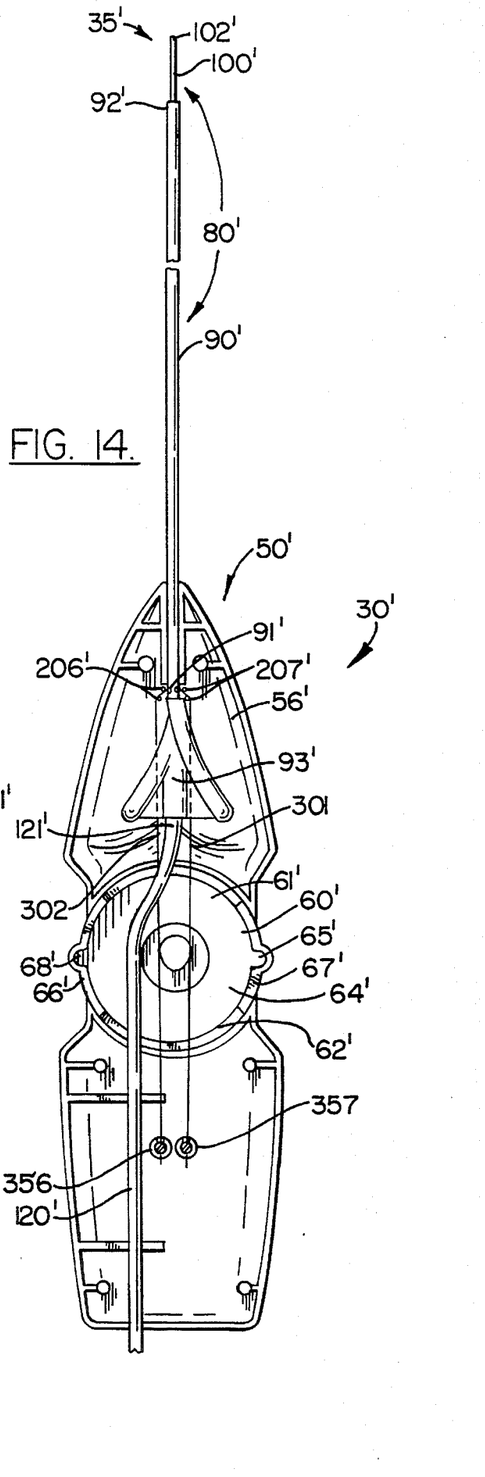
FIG. 14 is a bottom plan view of the steerable catheter according to the present invention with the bottom cover removed from the housing and with parts broken away for clarity illustrating another embodiment of the control means for the catheter.
Figure 15:
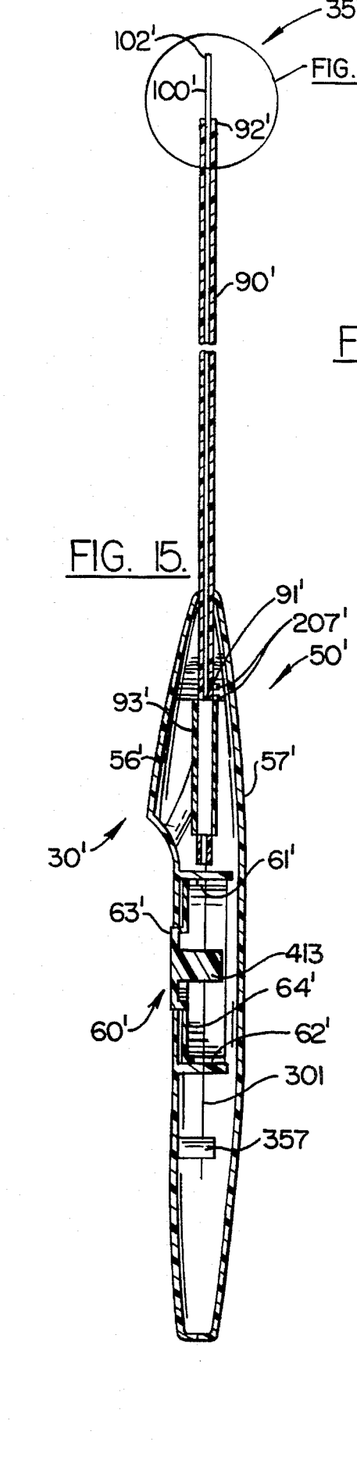
FIG. 15 is a side view of the steerable catheter according to the present invention with parts broken away for clarity illustrating another embodiment of the control means for the catheter.

FIGS. 13, 14 and 16 illustrate the engagement and connection of the guide wires 501, 502 of the other embodiment of the steerable catheter 335 to the control wheel 60' and housing 50'. The guide wires 501, 502 extend from the distal end 35', through the elongate tube means 40', and into the housing 50'. Inside the housing 50', the guide wires 501, 502 exit the elongate tube means 40', extend through the control wheel 60', and terminate into wire terminals 356, 357. The hub base 413 of the control wheel 60' of this embodiment is in the form of a cam which places tension on the guide wires 501, 502 when the control wheel 60' is rotated clockwise or counter-clockwise. The control wheel 60' is located within the housing 50' in a center portion thereof for laterally moving the guide wires 501, 502 to thereby control the flexible outer end portion of the tube means 80' by moving the guide wires 501, 502. The cam hub base 413 depending from a center portion of the control wheel 60, bears against and laterally displaces the portions of the guide wires 501, 502 adjacent the cam hub base 413 so that the guide wires 501, 502 are urged longitudinally and thereby move the flexible outer end portion.

Figure 19:
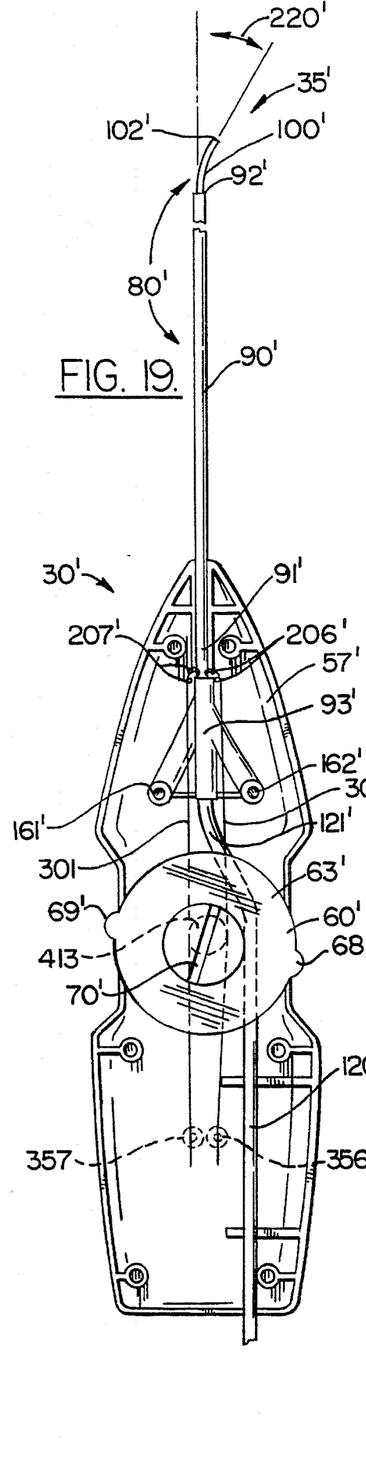
FIG. 19 is a top view with the top cover of the housing removed therefrom according to another embodiment of the present invention and illustrating the movement to the flexible outer end portion of the elongate tube means of the steerable catheter.
Figure 20:
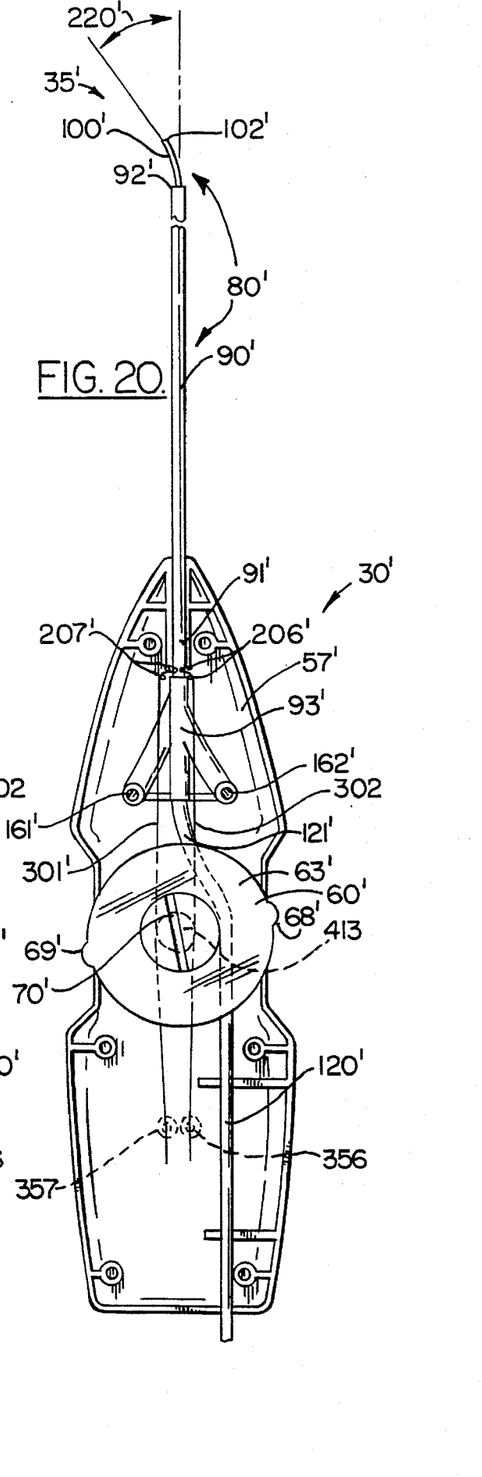
FIG. 20 is a top view with the top cover of the handle member removed therefrom according to another embodiment of the present invention and illustrating the movement to the flexible outer end portion of the elongate tube means of the steerable catheter.

FIGS. 19 and 20 illustrate the rotation of the control wheel 60' to thereby cause movement and adjustments in the angular attitude 220, of the distal end 35, of the steerable catheter 30'. The engagement and connection of the guide wires 501, 502 in the distal tube 40, and the control wheel 360 provide the additional control for the distal end 35, of the steerable catheter In the drawings and specification, there have been disclosed typical preferred embodiments of the invention and, although specific terms are employed, they are used in a generic and descriptive sense only and not for the purposes of limitation, the scope of the invention being set forth in the following claims.

That which is claimed is:

1. A catheter for use in body vessels or cavities, comprising:

a housing having a clam-shell configuration and having side peripheries of a medial portion thereof inwardly recessed so as to define a generally hourglass shape to be readily held in the hand of a user for responsively manipulating the catheter;

elongate tube means having a proximal end connected to said housing and extending outwardly therefrom and being formed of a material having sufficient stiffness to maintain said elongate tube means in a substantially straight condition in the absence of an external force being applied thereto, said elongate tube means having a flexible distal end portion and at least one lumen longitudinally extending from said distal end portion to said proximal end portion;

guide wires having proximal ends positioned within and connected to said housing and extending outwardly therefrom through said elongate tube means, distal ends of said guide wires being connected to said flexible distal end portion of said elongate tube means; and a control wheel rotatably mounted within said recessed medial portion of said housing, for engaging a portion of said guide wires so that rotation of said control wheel responsively moves said guide wires and thereby changes an angular attitude of said distal end portion of said elongate tube means.

2. A catheter according to claim 1 wherein said housing comprises a top cover having a plurality of fasteners integrally formed within said top cover, and a bottom cover having a corresponding plurality of fasteners integrally formed within said bottom cover, said plurality of corresponding fasteners cooperating to secure said top cover and said bottom cover along a longitudinal axis of said housing.

3. A catheter according to claim 2 further comprising a directional indicator visible on said top cover to indicate the angular attitude of said distal end portion of said elongate tube means.

4. A catheter according to claim 1 wherein said housing further comprises a plurality of access ports positioned in an outer surface of said housing to provide access to interior portions of said housing and to said at least one lumen.

5. A catheter according to claim 1 wherein said housing further comprises a top cover and a bottom cover, and wherein at least a major portion of said control wheel is encased between a top cover and a bottom cover in a medial portion of said housing.

6. A catheter according to claim 1 further comprising a manifold located within said housing, said manifold providing access to said elongate tube means.

7. A catheter for use in body vessels or cavities, comprising:

a housing having a clam-shell configuration, including a top cover, and having side peripheries of a medial portion thereof inwardly recessed so as to define a generally hourglass shape to be readily held in the hand of a user for responsively manipulating the catheter;

elongate tube means having a proximal end connected to said housing and extending outwardly therefrom and being formed of a material having sufficient stiffness to maintain said elongate tube means in a substantially straight condition in the absence of an external force being applied thereto, said elongate tube means having a flexible distal end portion and at least one lumen longitudinally extending from said distal end portion to said proximal end portion;

guide wires having proximal ends positioned within and connected to said housing and extending outwardly therefrom through said elongate tube means, distal ends of said guide wires being connected to said flexible distal end portion of said elongate tube means; and a control wheel rotatably mounted within said recessed medial portion of said housing, for engaging a portion of said guide wires so that rotation of said control wheel responsively moves said guide wires and thereby changes an angular attitude of said distal end portion of said elongate tube means.

8. A catheter according to claim 7 further comprising a directional indicator visible on a top cover to indicate the angular attitude of said distal end portion of said elongate tube means.

9. A catheter according to claim 7 wherein said housing further comprises a plurality of access ports positioned in an outer surface of said housing to provide access to interior portions said housing and to said at least one lumen.

10. A catheter according to claim 7 wherein at least a major portion of said control wheel is encased within said housing.

11. A catheter for use in body vessels or cavities, comprising:

a housing having a clam-shell configuration having side peripheries of a medial portion thereof inwardly recessed so as to define a generally hourglass shape to be readily held in the hand of a user for responsively manipulating the catheter, said clam-shell configuration formed from a top cover and a bottom cover secured along a longitudinal axis of said housing by a plurality of corresponding fasteners integrally formed in said top and bottom covers;

elongate tube means having a proximal end connected to said housing and extending outwardly therefrom and being formed of a material having sufficient stiffness to maintain said elongate tube means in a substantially straight condition in the absence of an external force being applied thereto, said elongate tube means having a flexible distal end portion and at least one lumen longitudinally extending from said distal end portion to said proximal end portion;

guide wires having proximal ends positioned within and connected to said housing and extending outwardly therefrom through said elongate tube means, distal ends of said guide wires being connected to said flexible distal end portion of said elongate tube means; and a control wheel rotatably mounted within said recessed medial portion of said housing, for engaging a portion of said guide wires so that rotation of said control wheel responsively moves said guide wires and thereby changes an angular attitude of said distal end portion of said elongate tube means.

12. A catheter according to claim 11 further comprising a directional indicator visible on said top cover to indicate the angular attitude of said distal end portion of said elongate tube means.

13. A catheter according to claim 11 wherein said housing further comprises a plurality of access ports positioned in an outer surface of said housing to provide access to interior portions said housing and to said at least one lumen.

* * * * *